(12) United States Patent
Kuusela et al.

(10) Patent No.: US 10,512,791 B2
(45) Date of Patent: Dec. 24, 2019

(54) METHODS TO OPTIMIZE COVERAGE FOR MULTIPLE TARGETS SIMULTANEOUSLY FOR RADIATION TREATMENTS

(71) Applicant: Varian Medical Systems International AG, Cham (CH)

(72) Inventors: Esa Kuusela, Espoo (FI); Emmi Ruokokoski, Helsinki (FI); Santtu Ollila, Helsinki (FI); Janne Nord, Espoo (FI); Jarkko Peltola, Suomi (FI)

(73) Assignee: Varian Medical Systems International AG, Cham (CH)

( * ) Notice: Subject to any disclaimer, the term of this patent is extended or adjusted under 35 U.S.C. 154(b) by 111 days.

(21) Appl. No.: 15/890,051

(22) Filed: Feb. 6, 2018

(65) Prior Publication Data

US 2019/0240507 A1 Aug. 8, 2019

(51) Int. Cl.
 *A61N 5/10* (2006.01)
(52) U.S. Cl.
 CPC ......... *A61N 5/1031* (2013.01); *A61N 5/1036* (2013.01); *A61N 5/1045* (2013.01); *A61N 5/1069* (2013.01)
(58) Field of Classification Search
 CPC .. A61N 5/1031; A61N 5/1036; A61N 5/1045; A61N 5/1069
 See application file for complete search history.

(56) References Cited

U.S. PATENT DOCUMENTS

| | | | | |
|---|---|---|---|---|
| 2005/0111621 A1* | 5/2005 | Riker | ................... | A61N 5/1031 378/65 |
| 2008/0081991 A1* | 4/2008 | West | ................... | A61N 5/1031 600/425 |
| 2016/0144201 A1 | 5/2016 | Schulte | | |
| 2017/0014642 A1 | 1/2017 | An et al. | | |
| 2018/0078792 A1* | 3/2018 | Ollila | ................... | A61N 5/1031 |
| 2018/0154179 A1* | 6/2018 | Ollila | ................... | A61N 5/1036 |
| 2018/0185669 A1* | 7/2018 | Kuusela | ................ | A61N 5/103 |
| 2018/0272152 A1* | 9/2018 | Kuusela | ................ | G06T 7/0012 |

OTHER PUBLICATIONS

European Application No. EP19155371.8, "Extended European Search Report", dated Jul. 16, 2019, 6 pages.
Schlaefer et al., "Stepwise Multi-Criteria Optimization for Robotic Radiosurgery", Medical Physics, vol. 35, Issue No. 5, May 2008, pp. 2094-2103.

* cited by examiner

*Primary Examiner* — Mark R Gaworecki
(74) *Attorney, Agent, or Firm* — Kilpatrick Townsend & Stockton LLP

(57) ABSTRACT

A cost function is constructed so as to guide an optimization process to achieve similar coverage for all targets simultaneously in a concurrent radiation treatment of multiple targets, so that a single scaling factor may be used in a plan normalization to achieve the desired coverage for all the targets. The cost function includes a component that favors a solution that attains similar target coverages for all targets, as well as a component that favors a solution that approaches the desired target coverage value for each individual target. The cost function includes a max term relating to deficiencies of actual target coverages with respect to a desired target coverage, or alternatively a soft-max term relating to deviations of actual target coverages with respect to an average target coverage, as well as to deficiencies of actual target coverages with respect to a desired target coverage.

20 Claims, 14 Drawing Sheets

METHODS TO OPTIMIZE COVERAGE FOR MULTIPLE TARGETS SIMULTANEOUSLY FOR RADIATION TREATMENTS

FIELD

The present disclosure relates generally to treatment planning for radiation therapy using external-beam radiation treatment systems, and is more particularly relates to optimizing coverage for multiple targets simultaneously.

BACKGROUND

Modern radiation therapy techniques include the use of Intensity Modulated Radiotherapy ("IMRT"), typically by means of an external radiation treatment system, such as a linear accelerator, equipped with a multi-leaf collimator ("MLC"). Use of multi-leaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom IMRT and other complex radiotherapy techniques, such as volumetric modulated arc therapy (VMAT, where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available techniques to develop and optimize a radiation treatment plan.

One of the common criteria for radiation treatment planning may be that a target volume attains the target coverage prescribed thereto. For example, a target coverage may be expressed by a statement that "at least 98% of the target volume should be covered by the prescribed dose level of 40 Gy." In practice, a target coverage may be enforced by a separate plan normalization step after an optimization has been performed based on other dosimetric criteria, where the dose level is scaled by adjusting the number of monitor units (MU) associated with the optimized control point sequence.

In cases where a tumor has metastasized, there may be multiple treatment targets within a treatment area of a patient. In concurrent treatment of multiple targets, the plan normalization solution may be sub-optimal, since a treatment plan may have different target coverages for different targets so that a single scaling factor may not be able to correct the target coverages for all targets.

Therefore, it is desirable to have optimization techniques that can attain uniform target coverages for multiple targets simultaneously in radiation treatment planning.

SUMMARY

According to some embodiments, a cost function may be constructed so as to guide an optimization process to achieve similar coverage for all targets simultaneously in a concurrent radiation treatment of multiple targets, so that a single scaling factor may be used in a plan normalization to achieve the desired coverage for all the targets. The cost function may include a component that favors a solution that attains similar target coverages for all targets, as well as a component that favors a solution that approaches the desired target coverage value for each individual target. In some embodiments, the cost function may include a max term relating to deficiencies of actual target coverages with respect to a desired target coverage. In some other embodiments, the cost function may include a soft-max term relating to deviations of actual target coverages with respect to an average target coverage, as well as to deficiencies of actual target coverages with respect to a desired target coverage. Such cost functions may favor a solution in which the target coverages for all targets "bundle" together at a common value that approaches the desired target coverage value. Even though the common value may be below the desired target coverage value, a single scaling factor may be used in a plan normalization to achieve the desired coverage for all the targets.

According to some other embodiments, instead of using a closed-form cost function, an iterative proportional integral (PI) controller-type approach is implemented in an optimization algorithm. This approach may automate the attainment of equal target coverage among multiple targets with lower objectives at the target-specific dose levels. In order to achieve this, a cost function can be modified during the optimization. The weights and the values for target lower dose objectives can be internally modified so as to push the target coverages towards the desired value. In this approach, because the desired value for the target coverages is automatically attained, no plan normalization is needed.

Other embodiments are directed to systems and computer readable media associated with methods described herein.

A better understanding of the nature and advantages of embodiments of the present invention may be gained with reference to the following detailed description and the accompanying drawings.

TERMS

Figure 1:
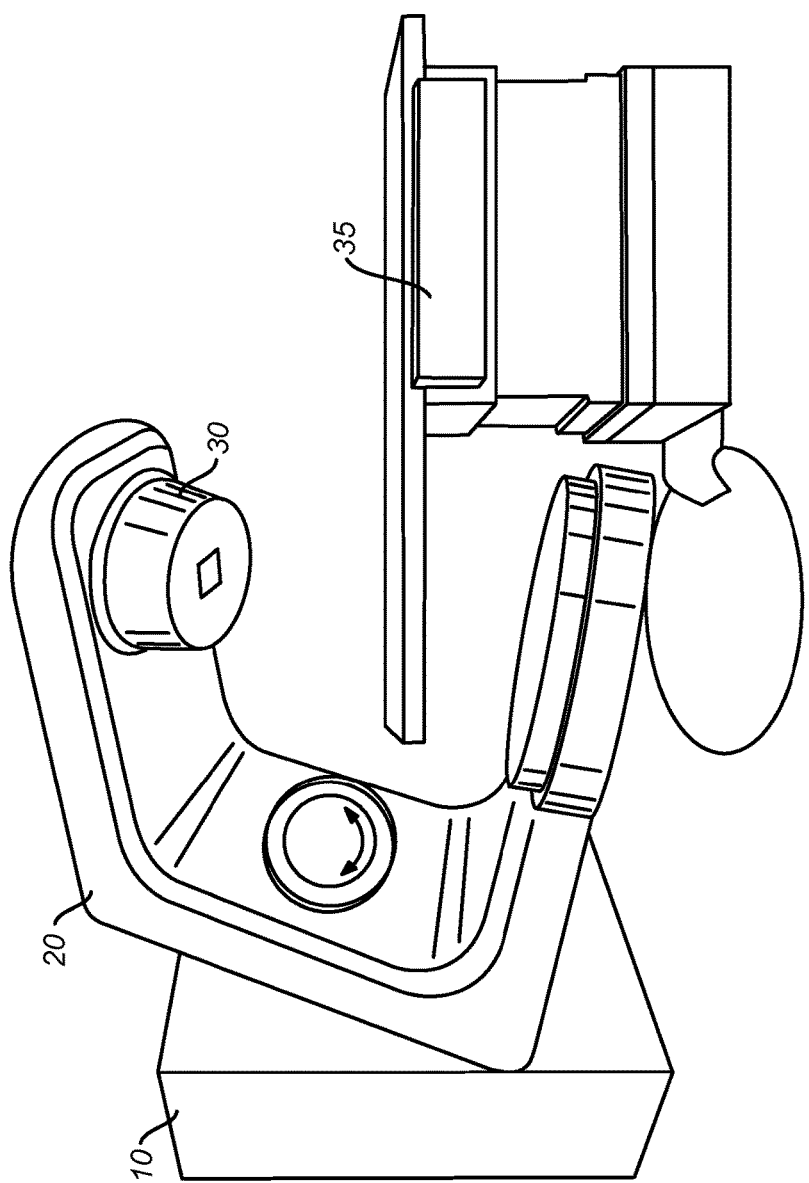
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the dose of radiation with position. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

"Beam's eye view" (BEV) is an imaging technique that can be used in radiation therapy for quality assurance and planning of external beam radiation therapy treatments. A BEV image can contain the images of a patient's anatomy and beam modifiers (such as jaws or multi-leaf collimators).

"Monitor unit" (MU) is a measure of machine output from a clinical accelerator for radiation therapy such as a linear accelerator. Monitor units are measured by monitor chambers, which are ionization chambers that measure the dose delivered by a beam and built into the treatment head of radiotherapy linear accelerators. Linear accelerators are calibrated to give a particular absorbed dose under particular conditions, although the definition and measurement configuration will vary between centers.

The term "control point" refers to a geometrical point associated with a set of values for treatment axes coordinates of an external-beam radiation treatment system, as well as the MU count and/or the related concept of the meterset weight. The treatment axes may include, but are not limited to, the isocenter, the position and angles of the patient support, the gantry angle, the collimator angle, and the position of each MLC leaf. The term "control point sequence" refers to a set of control points or a trajectory of control points in a static-gantry IMRT or in a rotating-gantry IMRT (also referred to as Volumetrically Modulated Arc Therapy, or VMAT).

DETAILED DESCRIPTION

The present disclosure relates generally to treatment planning for radiation therapy using external-beam radiation treatment systems, and is more particularly directed to optimizing coverage for multiple targets simultaneously. A cost function may be constructed so as to guide an optimization algorithm to achieve same coverage for all targets simultaneously in a concurrent radiation treatment of multiple targets, so that a single scaling factor may be used in a plan normalization to achieve the desired coverage for all the targets. In some embodiments, the cost function may include a max term relating to deficiencies of actual target coverages with respect to a desired target coverage. In some other embodiments, the cost function may include a soft-max term relating to deviations of actual target coverages with respect to an average target coverage, as well as to deficiencies of actual target coverages with respect to a desired target coverage. In some further embodiments, instead of using a closed-form cost function, an iterative proportional integral (PI) controller-type approach is implemented in an optimization. This approach may automate the attainment of equal target coverage among multiple targets with lower objectives at the target-specific dose levels, and hence no manual normalization step is required.

I. Treatment System

In general, radiation therapy includes the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used. External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
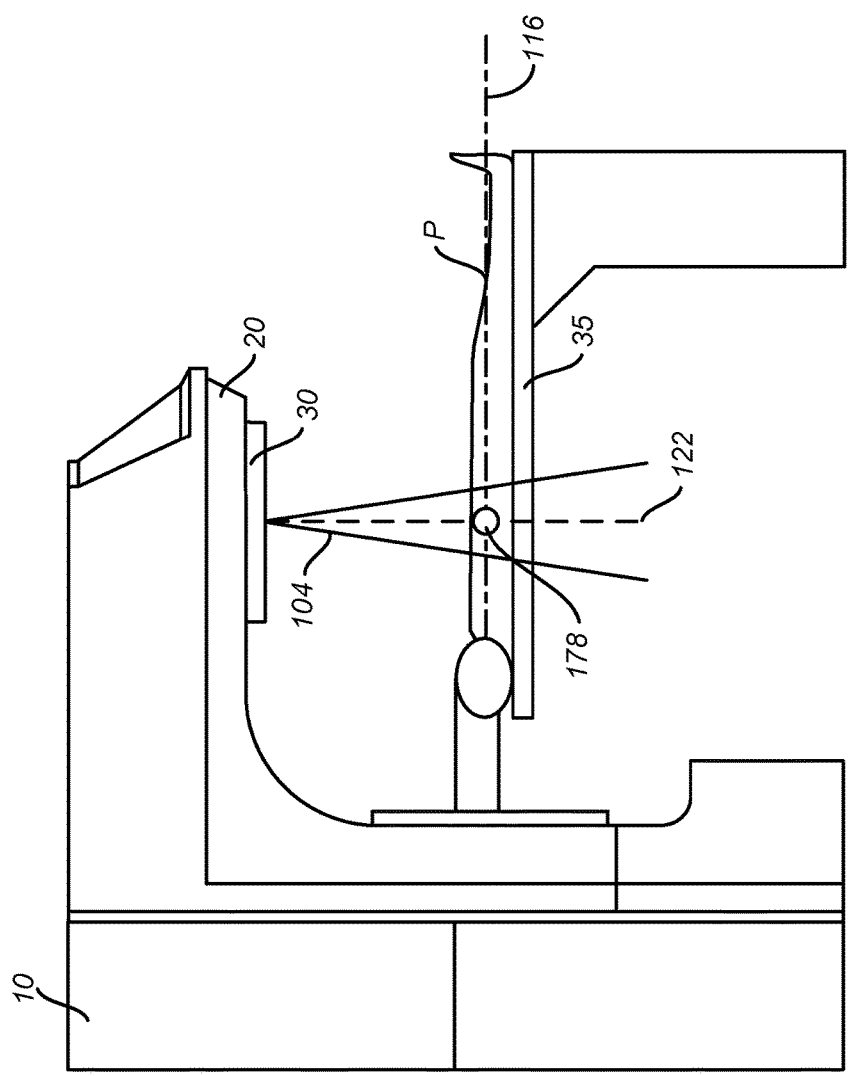
FIG. 2 is a schematic side view of a radiation treatment system.

FIGS. 1 and 2 depict a radiation treatment system of the type that may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178. It should be appreciated that radiation treatment systems using other types of gantries, such as a ring gantry, may be used.

Figure 3:
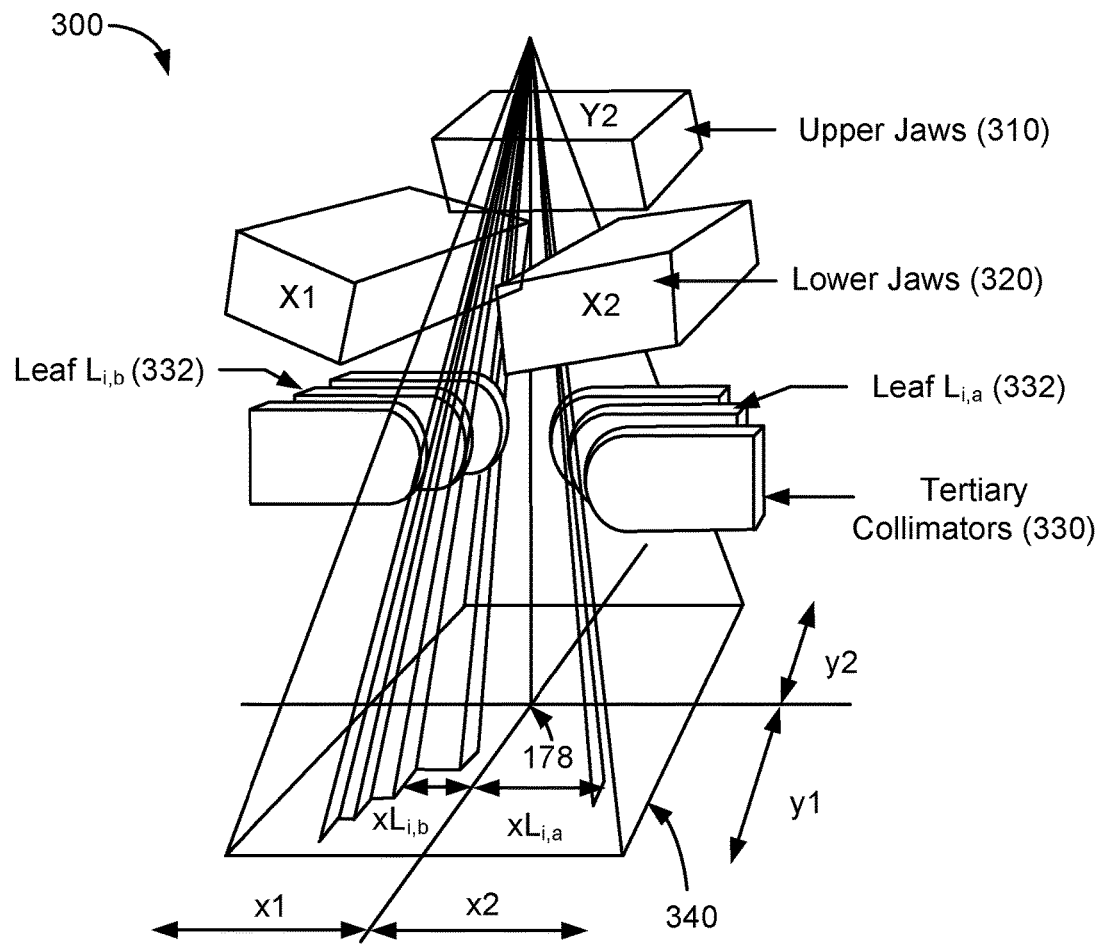
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multi-leaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. An example of a current MLC sold by the assignee of the present invention use up to 120 individually controllable leaves, typically thin slices of tungsten, that can be moved into or out of the x-ray beam under the control of system software.

Figure 4:
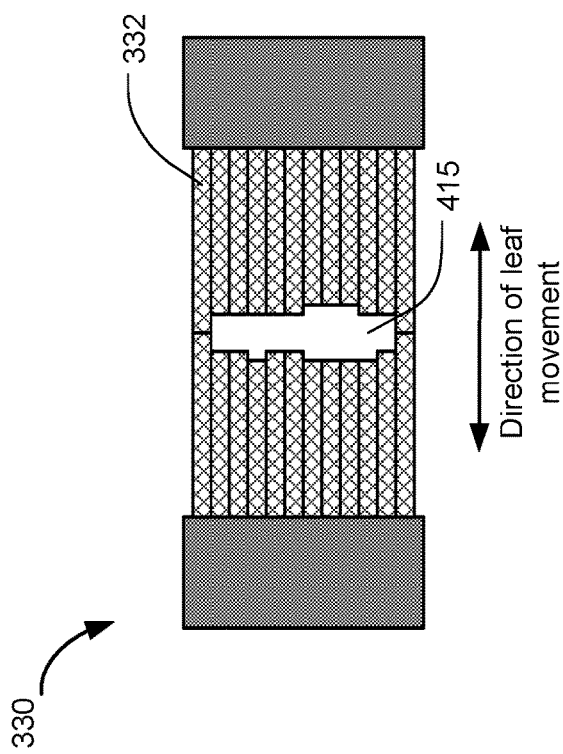
FIG. 4 shows an exemplary multi-leaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequences of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
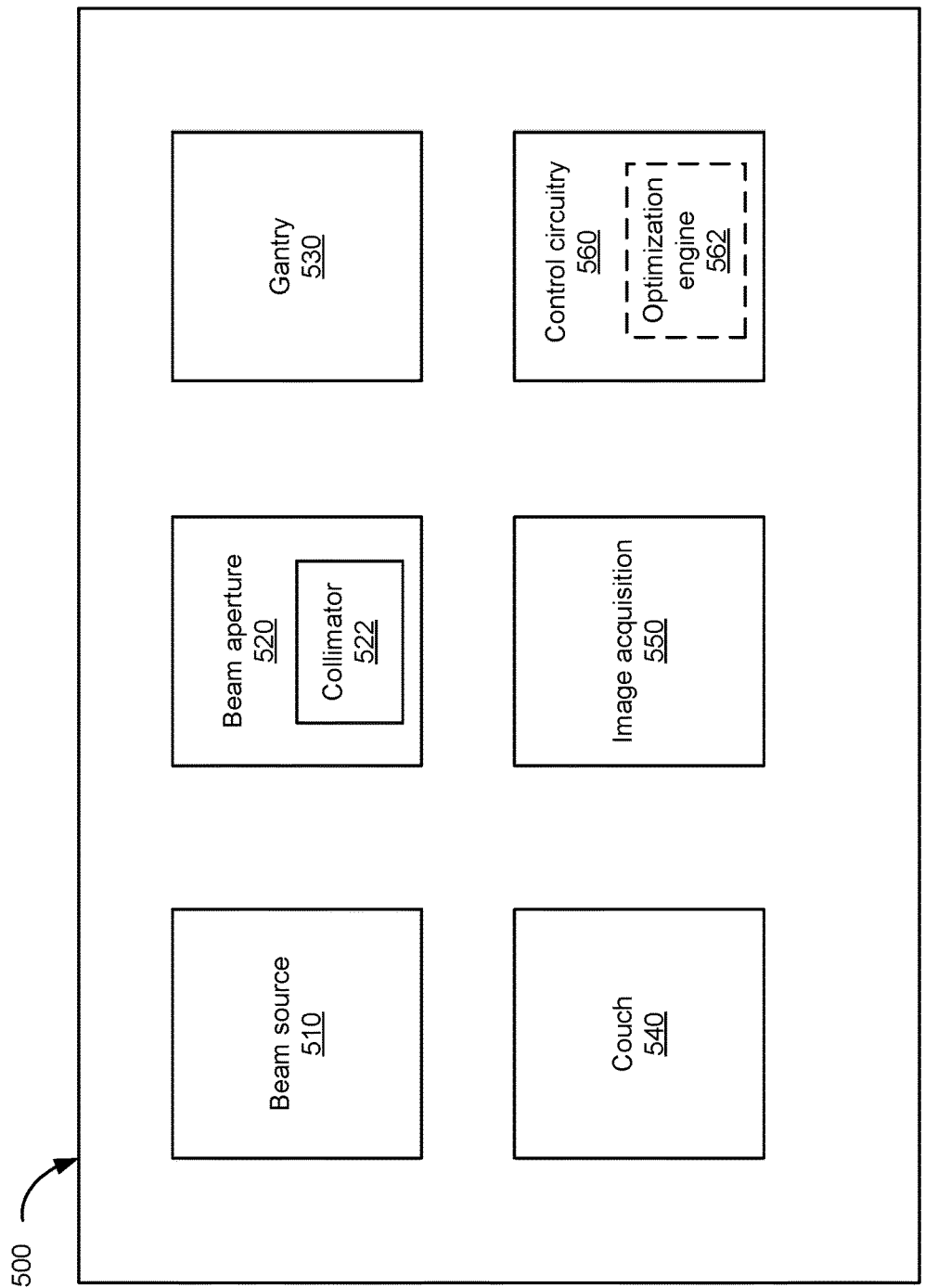
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various tradeoffs inherent in a radiation treatment plan, along with constraints that must be met for the radiation treatment plan to be medically acceptable or physically possible.

Treatment planning algorithms can account for the capabilities of the specific radiation treatment system they are used with, for example, the energy spectrum and intensity profile of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a tradeoff between the accuracy and speed of the different algorithms available for treatment planning.

III. Optimizing Coverage for Multiple Targets Simultaneously

The treatment planning of an Intensity Modulated Radiation Therapy (IMRT) may be performed using an optimization algorithm that seeks a particular treatment machine control point sequence that minimizes or maximizes the value of a user-given cost function. A constraint optimization is the process of optimizing an objective function with respect to some variables in the presence of constraints on those variables. The objective function is either a cost function or energy function which is to be minimized, or a reward function or utility function, which is to be maximized. Constraints can be either hard constraints which set conditions for the variables that are required to be satisfied, or soft constraints which have some variable values that are penalized in the objective function if, and based on the extent that, the conditions on the variables are not satisfied.

Optimization algorithms may be used in both the static-gantry IMRT and the rotating-gantry IMRT (also referred to as Volumetrically Modulated Arc Therapy, or VMAT). The cost function may include terms that depend on certain dosimetric aspects of a radiation treatment plan, such as dose-volume-histograms (DVHs) or dose distribution in general. For example, the cost function may include terms relating to the minimum dose for a planning target volume (PTV), the mean dose for an organ at risk (OAR), and the like.

A criterion for radiation treatment planning may be that a target volume attains the relative volumetric coverage prescribed thereto. For example, a relative volumetric coverage may be expressed by a statement that "at least 98% of the target volume should be covered by 100% of the prescribed dose level of 40 Gy." Herein, relative volumetric coverage may be referred to simply as target coverage. In practice, a target coverage may be enforced by a separate plan normalization step after an optimization has been performed based on other dosimetric criteria, where the dose level is scaled by adjusting the number of monitor units (MU) associated with the optimized control point sequence.

Figure 6:
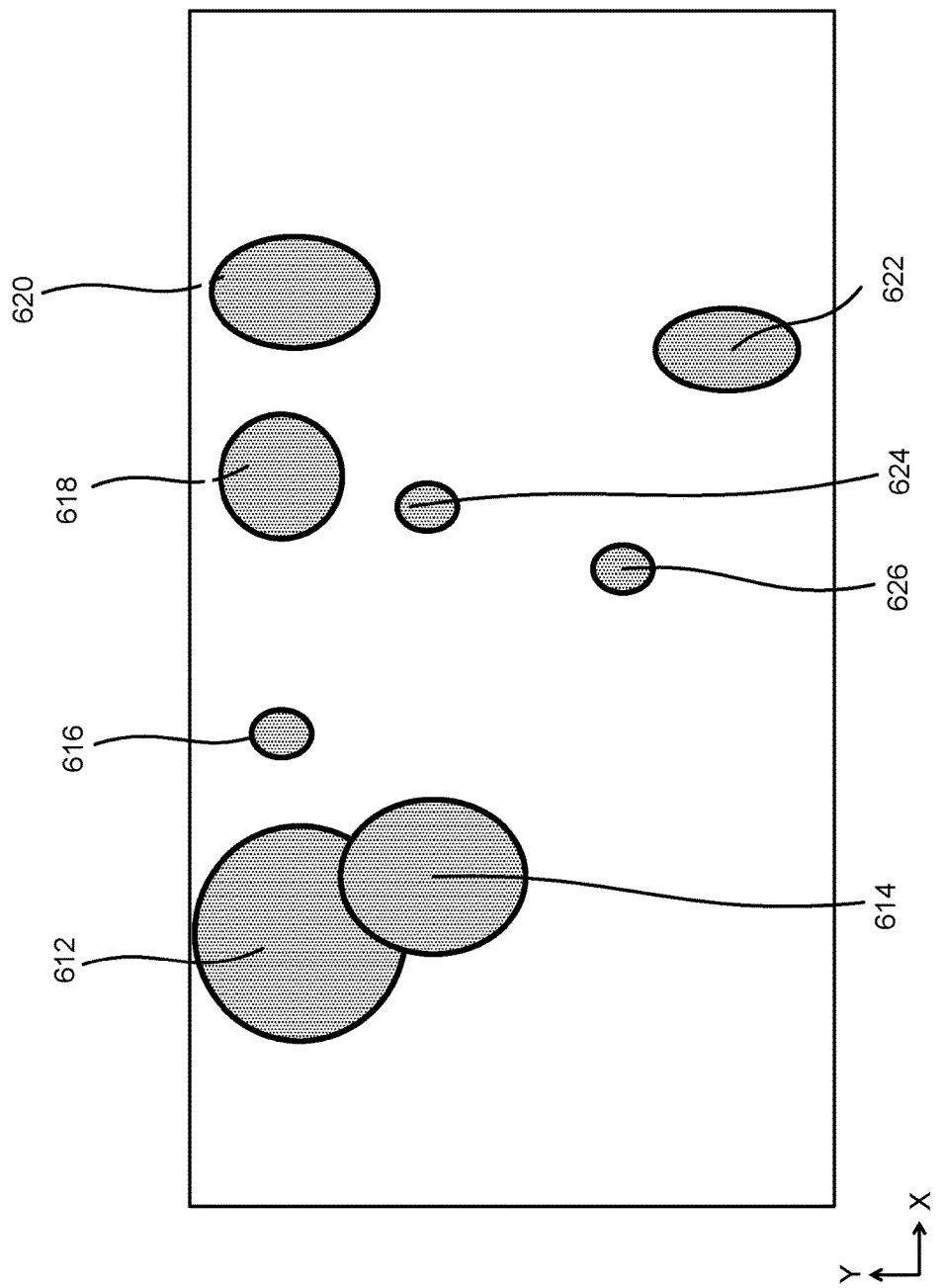
FIG. 6 shows an exemplary schematic beam's-eye view (BEV) of a treatment area (e.g., a cranial region) of a patient exhibiting multiple targets.

In cases where a tumor has metastasized, there may be multiple treatment targets within a treatment area of a patient. FIG. 6 shows an exemplary schematic beam's-eye view (BEV) of a treatment area (e.g., a cranial region) of a patient. As illustrated, there are a number of metastatic targets 612, 614, 616, 618, 620, 622, 624, and 626 in the treatment area. In concurrent treatment of multiple targets, the plan normalization solution may be sub-optimal, since a treatment plan obtained by an optimization algorithm may have different target coverages for different targets so that a single scaling factor may not be able to correct the target coverages for all targets, as discussed below.

Figure 7:
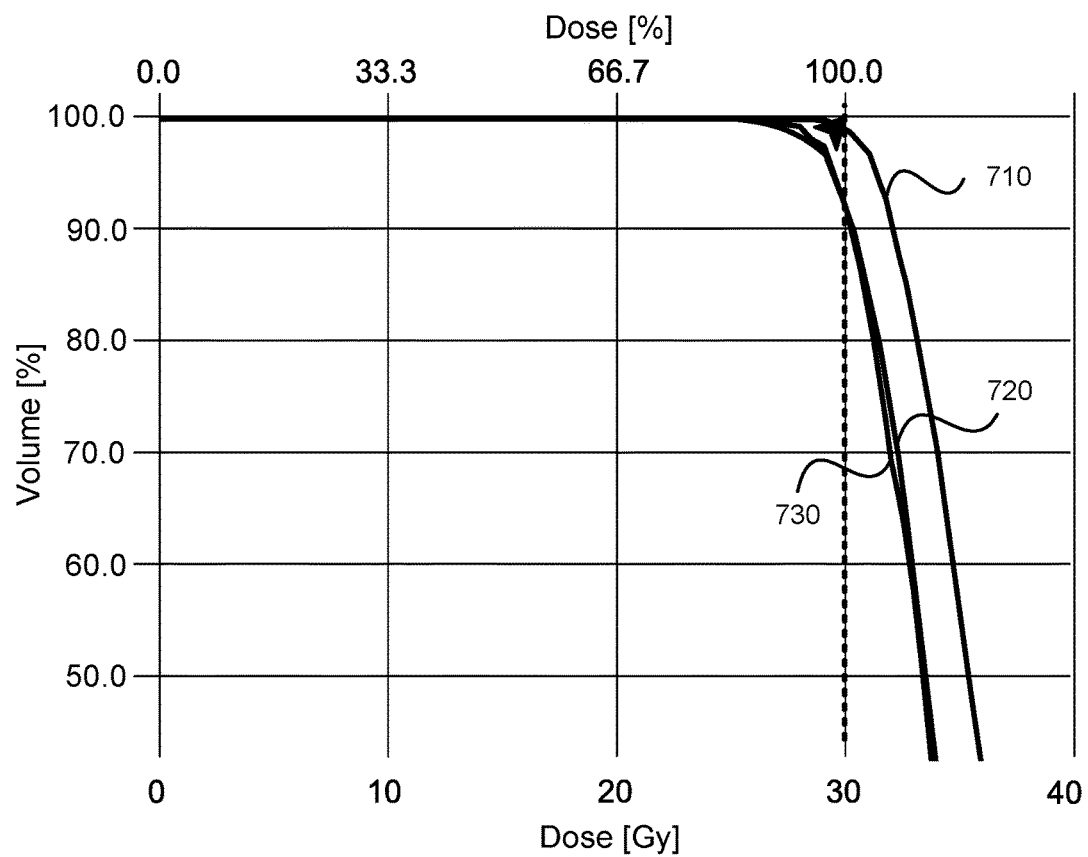
FIG. 7 shows exemplary dose volume histogram (DVH) curves for three brain metastasis targets of an optimized treatment plan.

FIG. 7 shows exemplary DVH curves 710, 720, and 730 for three brain metastasis targets of an optimized treatment plan. Each target has a lower objective of 30 Gy and 98% target coverage (i.e., 98% of the target volume should receive at least 30 Gy). As illustrated, although the target coverage for the first target, as indicated by the first DVH curve 710, is at or above the desired value of 98%, the target coverages for the second target and the third target, as indicated by the second DVH curve 720 and the third DVH curve 730, are below the desired value of 98%. Thus, a single scaling factor may not provide satisfactory results. For example, while a single scaling factor may bring the target coverages for the second target and the third target to 98%, it may result in over-dose for the first target.

One solution may be to normalize target coverage for each target individually. For example, individual normalization may be achieved by normalizing individual fields (e.g., individual VMAT arcs or individual IMRT control points), where certain fields deliver dose only to a sub-set of the targets. Such a solution, however, may result in an inefficient treatment plan (e.g., having longer treatment time), or can be impractical for a large number of targets.

Embodiments of the present invention provide solutions for achieving uniform target coverages for all targets during the optimization phase of an IMRT or VMAT treatment planning. This may be advantageous, as even if the common target coverage for all the targets is below the desired target coverage (e.g., the common target coverage for all targets is 94%, while the desired target coverage is 98%), a single scaling factor may be used in a plan normalization to achieve the desired coverage for all targets. The solutions may utilize certain forms of cost functions that penalize the differences in achieved target coverages among multiple targets in an optimization algorithm.

A. Cost Functions

An optimization algorithm may try to find a control point sequence $\{L\}$ that minimizes a cost function $C(\{L\})$, where the control point sequence $\{L\}$ instructs a radiation treatment machine in dose delivery. The control point sequence $\{L\}$ may also include multileaf collimator (MLC) sequences. A cost function may be constructed as a sum of several cost terms. For instance, an exemplary cost function may be expressed as:

$$C(\{L\}) = \Sigma_{i \in T_<} w_i [\hat{V}_D^i - V_D^i(\{L\})]^2 + \Sigma_{j \in \{T>, OAR>, \ldots\}} c_j(\{L\}). \quad \text{Eq. (1)}$$

The first summation in Eq. (1) may represent those cost terms relating to target coverages. For example, $\hat{V}_D^i$ may represent a user-defined goal value of the target coverage for target i, and $V_D^i(\{L\})$ may represent the value of the target coverage for target i calculated based on a particular control point sequence $\{L\}$ in an iteration of an optimization. The symbol "T<" may represent target lower dose objectives of a treatment plan (e.g., the minimum target coverage should be 98%). In some embodiments, each of the cost terms relating to target coverages may be expressed as a quadratic function of the positive difference between the goal coverage value $\hat{V}_D^i$ and the calculated coverage value $V_D^i(\{L\})$ based on a particular control point sequence $\{L\}$, (i.e., the deficiency of the calculated coverage value with respect to the goal coverage value), as shown in Eq. (1). Each quadratic term may be multiplied by a weight $w_i$ corresponding to a relative importance of the term with respect to the other terms.

The second summation in Eq. (1) may represent those cost terms relating to other clinical goals for the treatment targets, as well as for any organs at risk (OARs). The symbol "T>" may represent upper dose objectives for the treatment targets (e.g., the maximum dose for a target). The symbol "OAR>" may represent upper dose objectives for any OARs (e.g., the maximum mean dose for an OAR). In general, as the delivered dose is increased, the first summation in Eq. (1) may decrease, while the second summation in Eq. (1) may increase. An objective of the optimization algorithm may be to search for a balance where any further increase or decrease in delivered dose does not reduce the value of the entire cost function. For concurrent radiation treatment of multiple targets, the cost function expressed in Eq. (1) does not include a direct mechanism that would guide an optimization algorithm to achieve same coverage for all the targets.

B. Max Cost Function

According to some embodiments, a cost function may be constructed so as to guide an optimization algorithm to achieve same coverage for all targets in a concurrent treatment of multiple targets, so that a single scaling factor may be used in a plan normalization to achieve the desired coverage for all the targets. An exemplary cost function may be expressed as follows:

$$C = w \cdot \max_i [\hat{V}_D^i - V_D^i]^2 + \sum_{j \in \{T>, OAR>, \ldots\}} c_j. \quad \text{Eq. (2)}$$

In Eq. (2), the first summation in Eq. (1) is replaced with a maximum of all the individual cost terms relating to target coverages. The cost function expressed in Eq. (2) may be referred herein as a max cost function. With the max cost function, a decrease in delivered dose may not increase the value of the cost function unless it either causes the target that currently has the worst dose coverage to have an even worse dose coverage, or it causes another target to have a dose coverage that is worse than the current worst dose coverage. As such, the max cost function may favor a solution in which the target coverages for all targets "bundle" together at the poorest coverage. The max cost function may also favor a solution that attains a common target coverage approaching the desired target coverage value for each individual target by virtue of the term max $[\hat{V}_D^i - V_D^i]^2$, as greater differences may incur a greater penalty (i.e., more cost). Thus, the max function may bundle the DVH curves together to a common target coverage value, and the term max $[\hat{V}_D^i - V_D^i]^2$ may push the common value to a desired target coverage level.

It should be noted that the max cost function expressed in Eq. (2) may be applied to cases where the desired target coverages vary for different targets (e.g., at least 95% of the first target volume should receive 100% of the prescribed dose of 30 Gy, and at least 98% of the second target volume should receive 100% of the prescribed dose of 30 Gy). In practice, the desired target coverages for various targets may be the same (e.g., at least 98% of the target volume should receive 100% of the prescribed dose of 30 Gy for all target volumes).

The max cost function expressed in Eq. (2) may cause unstable behavior in an optimization process in some cases. An efficient optimization process may rely on sampling the space of all possible control point sequences efficiently. Efficient sampling may be achieved, for example, by calculating the gradient of a cost function with respect to the control point parameters (i.e., changes in the cost function due to small changes in the control point parameters), in order to determine what changes in the control point parameters should be made for the current iteration. For the max cost function, small changes in the control point parameters may not affect the gradient unless they affect the poorest coverage. For example, the max cost function may be relatively insensitive to situations where the maximum value is only slightly greater than the next largest term. Thus, even a small change in the direction of the cost function gradient can actually make the solution worse.

C. Soft-Max Cost Function

According to some other embodiments, to facilitate the calculation of the cost function gradient, a cost function may be constructed as a soft-max function as follows:

$$C = \sum_{i \in T_<} w_i \frac{e^{w_i \vartheta}}{G} [\hat{V}_D^i - V_D^i]^2 + \sum_{j \in \{T>, OAR>, \ldots\}} c_j, \quad \text{Eq. (3)}$$

where $$\vartheta = \frac{\overline{V}_D - V_D^i}{\alpha}, \quad G = \sum_{i \in T_<} e^{w_i \vartheta},$$

where $\overline{V}_D$ is the mean target coverage of all targets and the alpha parameter is a scale of the soft-max core describing how large variations from the average value are acceptable.

The soft max cost function expressed in Eq. (3) may penalize strongly for deviations from the mean value $\overline{V}_D$ by virtue of the exponential term $e^{w_i \vartheta}$, and thus may push the target coverages for all targets toward the mean value. Similar to the max cost function, the term $[\hat{V}_D^i - V_D^i]^2$ may favor a solution that attains a common target coverage approaching the desired value of the target coverage for each individual target. Unlike the max cost function expressed in Eq. (2), however, the value of the soft-max cost function may be affected by small changes in the control point parameters. This is because, even though the term relating to the target with the worst coverage may have a dominant effect on the value of the first summation by virtue of the exponential function, the terms relating to other targets still contribute to the value of the first summation. Therefore, the soft-max cost function may facilitate a more stable optimization process.

Figure 8:
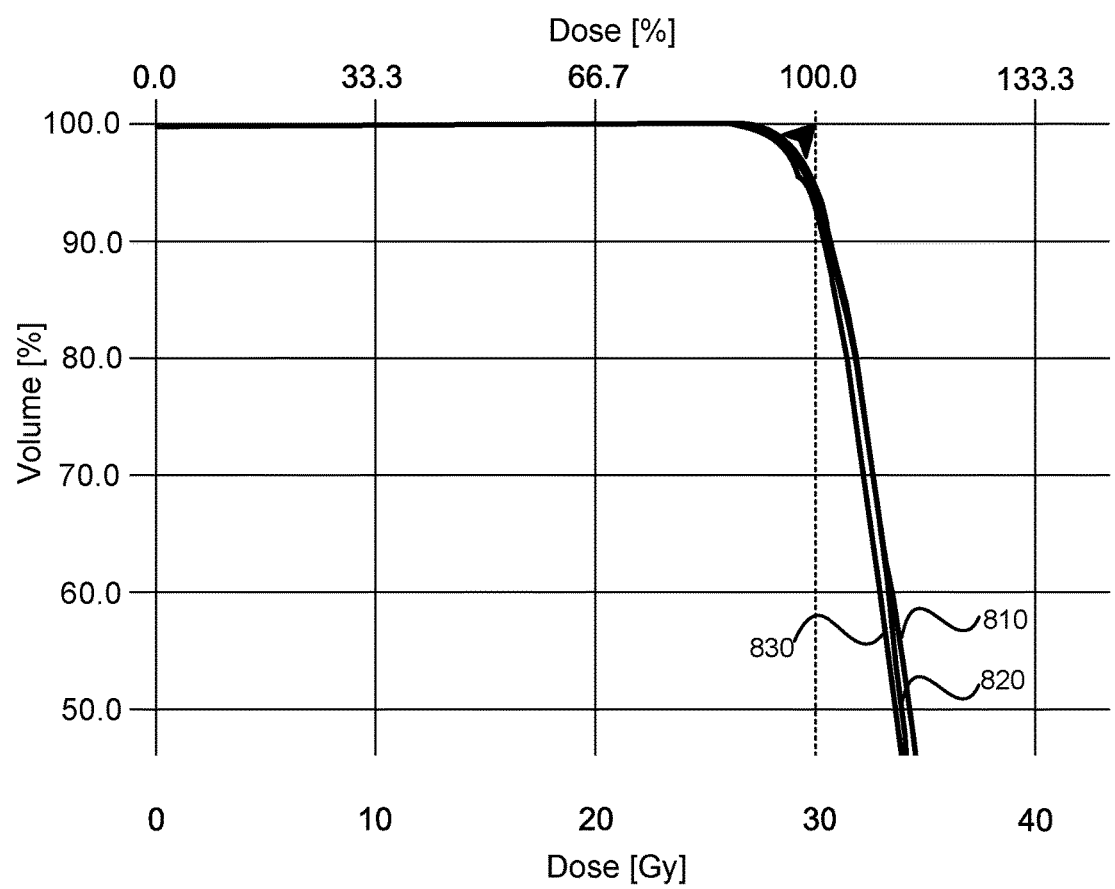
FIG. 8 shows exemplary DVH curves for the same three brain metastasis targets illustrated in FIG. 7, but of a treatment plan obtained using a soft-max cost function according to some embodiments of the present invention.

FIG. 8 shows exemplary DVH curves 810, 820, and 830 for the same three brain metastatic targets illustrated in FIG. 7, but of a treatment plan obtained using the soft-max cost function as expressed in Eq. (3) according to some embodiments. As illustrated, the target coverages for the three targets have a similar value of about 94%. In other words, the DVH curves are "bundled" together at a common target coverage value of 94%. Therefore, even though the common target coverage value is below the desired value of 98%, a single scaling factor may be used in a plan normalization to achieve the desired coverage for all the targets.

D. More Detailed Cost Functions

According to some embodiments, the terms in the soft-max cost function expressed in Eq. (3) may be modified in order to control in greater detail how different target coverages are scored relative to other clinical goals. For example, it may be beneficial to have the cost function gradient to be more sensitive to the details of the dose distribution at each target volume. This can be advantageous in a situation where a small target volume is discretized such that the evaluation of target coverage may be based only on a few dose sampling points. In such a situation, it may be beneficial to formulate the cost function such that a significant amount of the dose sampling points actually contribute to the cost even though they do not have a direct impact on the requested target coverage.

In some embodiments, the term $\lfloor \hat{V}_D^i - V_D^i \rfloor^2$ in the soft-max cost function expressed in Eq. (3) may be replaced with:

$$\lfloor \hat{V}_D^i - V_D^i \rfloor^2 \sum_{k \in V_{T_i}} \lfloor D_i - d_k \rfloor^2, \qquad \text{Eq. (4)}$$

where $d_k$ is the dose at location k belonging to target i, and $D_i$ is an internally defined goal dose value that may be somewhat greater than the prescribed target dose level (e.g., if the lower dose objective is 24 Gy for target i, $D_i$ may be defined as 26 Gy). The term expressed in Eq. (4) may allow more sampling points in a target volume.

E. Automatic Lower Dose Objective

The max cost function of Eq. (2) or the soft-max cost function of Eq. (3) described above may have problems with convergence, where the value of the cost function may change drastically between iterations. This can cause the optimizer to get stuck; i.e, the optimizer cannot find any new control point sequences that would result in a lower cost. Such problems may arise from the fact that, for a small target, the value of the target coverage can vary significantly for small changes in the control point sequences. By including terms in the cost function that depend directly on the deviation of the calculated target coverage from the desired target coverage, such as the cost functions expressed in Eq. (2) and Eq. (3), those terms may dictate the optimization. For example, the term $e^{w_i \vartheta}$ in Eq. (3), where $$\vartheta = \frac{\overline{V}_D - V_D^i}{\alpha},$$

can cause a cost term from a single target to be the dictating contribution in the cost function due to a small deviation from the desired target coverage value.

According to some embodiments, instead of using a closed-form cost function, an iterative proportional integral (PI) controller-type approach is implemented in an optimization. This approach may automate the attainment of equal target coverage among multiple targets with lower objectives at the target-specific dose levels. In other words, this approach may bundle the target DVHs so that the same relative volume is covered by the prescribed target dose level for all the targets. In order to achieve this, a cost function, such as the cost function expressed in Eq. (1), is modified at each iteration during the optimization. The weights, as well as the dose values for target lower dose objectives, may be internally modified between iterations so as to push the target coverages towards the desired value. In this approach, because the desired value for the target coverages is automatically attained, no plan normalization may be needed. This approach is referred herein as automatic lower dose objective (ALDO).

In this approach, as the cost function is evaluated, a check is performed for each respective target to determine whether the target coverage for the respective target is below or above the desired value. The weight and the dose value of the target lower dose objective for the respective target is adjusted (increased or decreased) accordingly, thus modifying the cost function. In some embodiments, the sum of the weights for all targets $W = \Sigma w_i$ may be scaled up (or down) if the mean coverage is below (or above) the desired value. The change of W from the previous total weight is limited and the change to each individual target weight is added as a correction to the previous weight.

In some embodiments, the weight adjustment for target i at a respective iteration j may depend on the sum $S_i$ of deviations from the desired coverage value $V_D$ in the previous iterations j<j' as well as the current iteration j:

$$S_i = \Sigma_{j' \leq j} [V_D - V_i^{j'}], \qquad \text{Eq. (5)}$$

where $V_i^{j'}$ is the target coverage for target i evaluated at iteration j'.

In some embodiments, the weight adjustment for target i may also depend on the normalized deviation $\Delta_i$ of the current target coverage $V_i$ for target i from the current mean target coverage $\overline{V}$:

$$\Delta_i = [\overline{V} - V_i]/\max_k |\overline{V} - V_k|, \qquad \text{Eq. (6)}$$

where $V_k$ is the target coverage of target k that gives rise to the maximum deviation $|\overline{V} - V_k|$. Thus, the normalized deviation $\Delta_i$ is bounded between [−1, 1].

In some embodiments, at iteration j, the weight for target i may be given as:

$$w_i^j = \alpha[w_i^{j-1} + v_i(\Delta_i \sigma + S_i \sigma^2)] = \alpha \omega_i^j, \qquad \text{Eq. (7)}$$

where σ is the standard deviation of the target coverages $$\sigma = \sqrt{\overline{V^2} - \overline{V}^2},$$

$w_i^{j-1}$ is the weight for target i in the previous iteration, $v_i$ is a weight, and $\alpha$ is a scaling parameter. In some embodiments $$\alpha = \frac{w^j}{\sum_i \omega_i^j},$$

where w is the total weight $W^j = \Sigma w_i$ at iteration j. The initial weight $w_i^0 = v_i$. Note that if $v_i = 0$, $w_i = 0$.

The total weight $W^j$ may be scaled up or down from one iteration to the next if the mean coverage $\overline{V}$ is below or above the desired value. In some embodiments, the change of $W^j$ from the previous total weight is limited by an internally defined percentage of the total weight, so that the total weight does not change drastically from one iteration to another. This may ensure that the ALDO term in the cost function does not override all the other terms, so that the optimizer would not reach solutions that have uniform target coverage but otherwise a clinically unacceptable dose distribution.

In Eq. (7), by multiplying $S_i$ by $\sigma^2$ and $\Delta$ by $\sigma$, the correction to the cost function may approach zero when the target coverages approach the desired value $V_D$, which can ensure convergence of the optimization algorithm. The summation term $S_i$ to the weight adjustment in Eq. (7) may help the optimization process to find a solution that attains the desired target coverage value $V_D$ for each target. The normalized deviation term $\Delta_i$ in Eq. (7) may help finding a solution that attains equal target coverage among all targets. In Eq. (7), a quadratic dependence on cis chosen for the summation term $S_i$ so as to decrease the effect of this term for small values of $\sigma$. In some other embodiments, a linear dependence on $\sigma$ may be chosen for the summation term $S_i$. In some further embodiments, a quadratic dependence on $\sigma$ may be chosen for the normalized deviation term $\Delta_i$.

In some embodiments, for a cost function that includes terms similar to those expressed in Eq. (4), the value of the target lower dose objective for each respective target may also be iteratively adjusted as:

$$d_i^j = d_i^{j-1}[1.0 + (V_D - V_i)], \quad \text{Eq. (8)}$$

where $d_i^{j-1}$ is the value of the target lower dose objective for target i in the previous iteration j-1.

Figure 9:
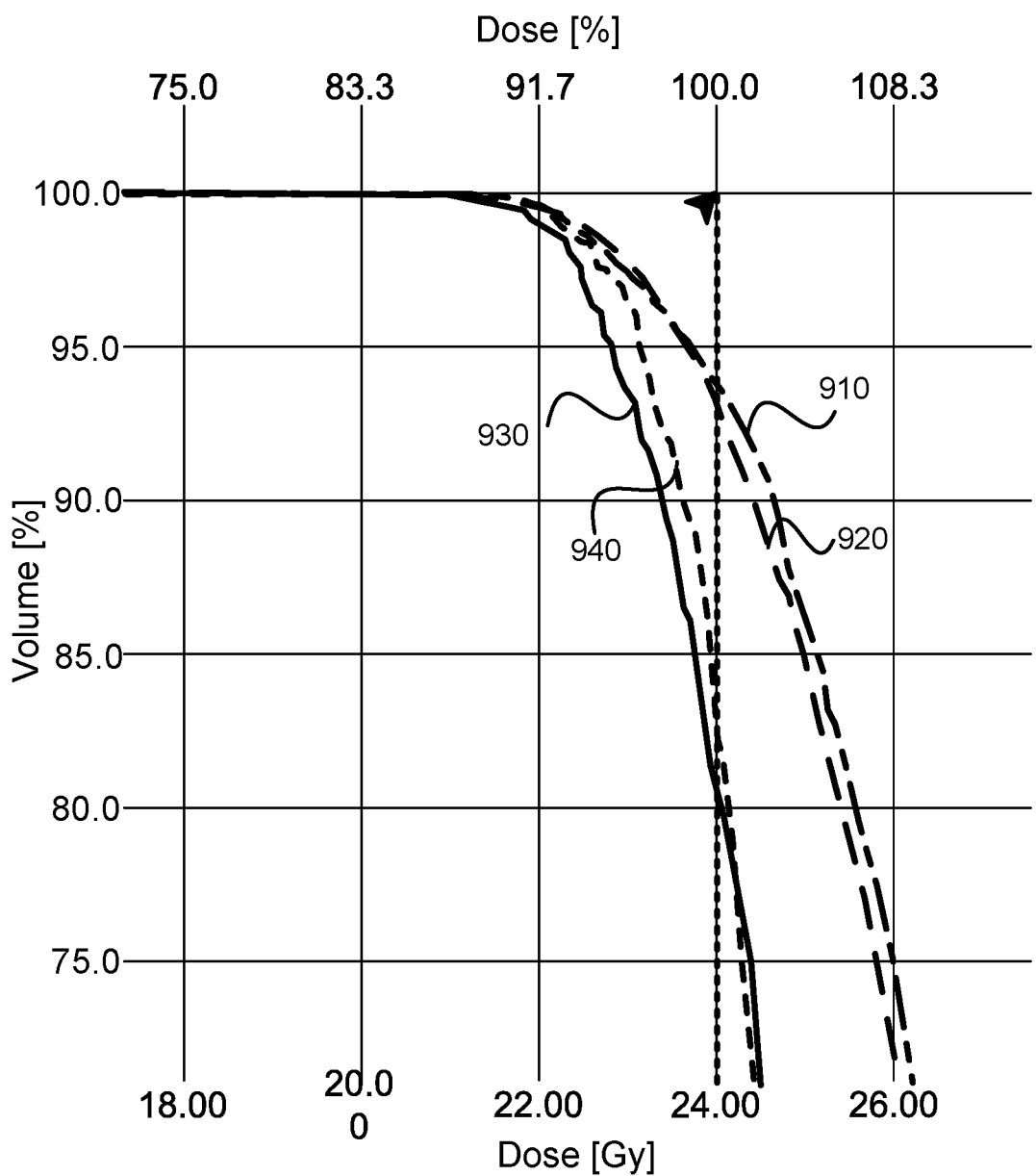
FIG. 9 shows exemplary DVH curves for four brain metastasis targets of an optimized treatment plan.

FIG. 9 shows exemplary DVH curves 910, 920, 930, and 940 for four brain metastasis targets of a treatment plan optimized using a convention optimization algorithm. Each target has a lower objective of 24 Gy and 98% volume (i.e., 98% of the target volume should receive at least 24 Gy). As illustrated, the target coverage for each of the four targets is below the desired target coverage of 98%. Thus, a plan renormalization may be necessary in order to reach the desired target coverage. Furthermore, the target coverages for the four targets are different from each other. For example, the target coverages for the first target and the second target, as indicated by the DVH curves 910 and 920, are in a range from 93% to 95%, whereas the target coverages for the third target and the fourth target, as indicated by the DVH curves 930 and 940, are in a range from 80% to 83%. Thus, a single scaling factor may not provide satisfactory results.

Figure 10:
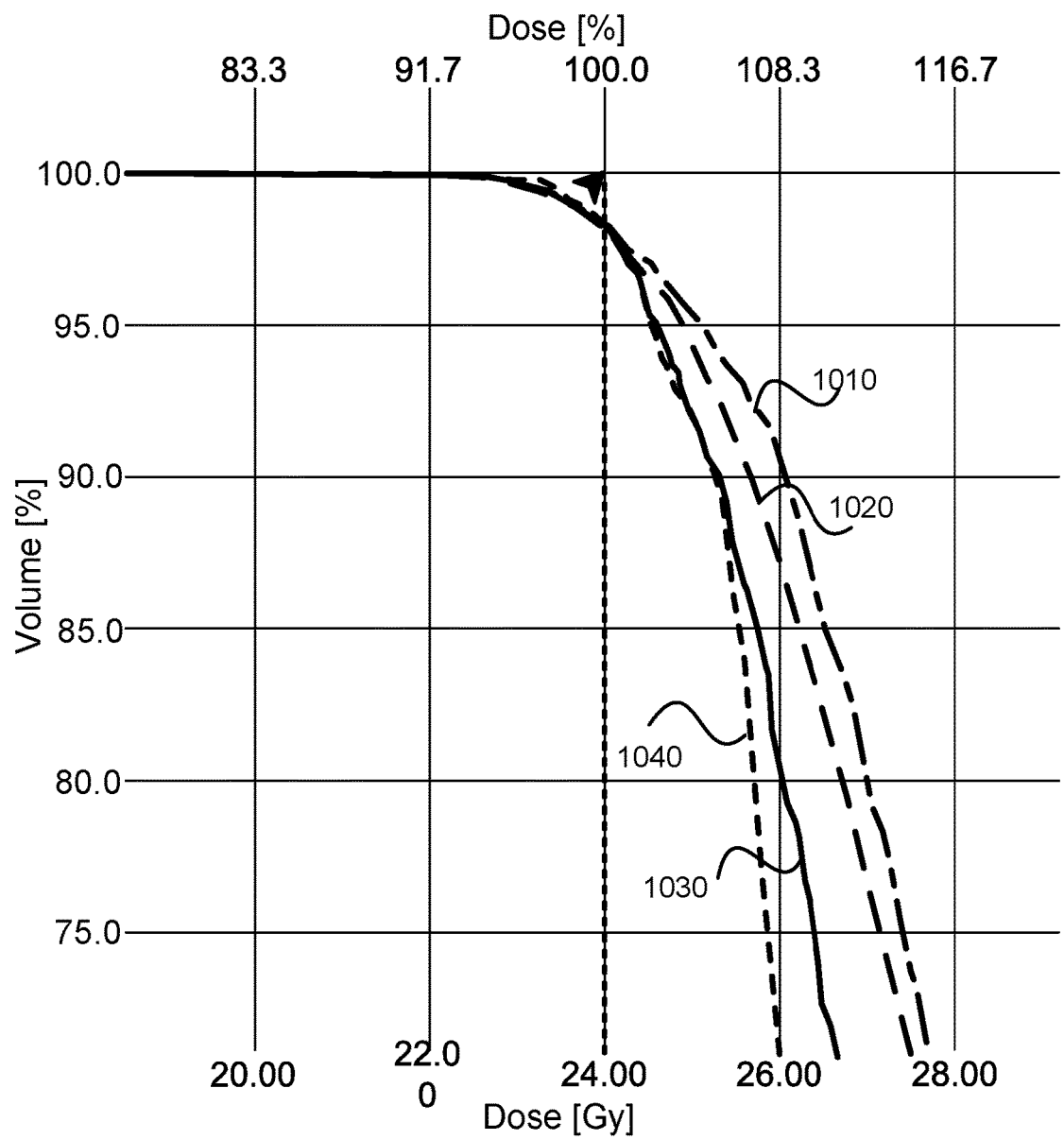
FIG. 10 shows exemplary DVH curves for the same four brain metastasis targets illustrated in FIG. 9, but of an optimized treatment plan using an iterative proportional integral (PI) controller-type approach to the cost function according to some embodiments of the present invention.

FIG. 10 shows exemplary DVH curves 1010, 1020, 1030, and 1040 for the same four brain metastasis targets of a treatment plan optimized using ALDO as described above according to some embodiments. As illustrated, the target coverages at 24 Gy for the four targets have approximately the same value of 98%, which is the desired target coverage value. Thus, the ALDO optimization algorithm bundles the target DVHs so that the same relative volume is covered by the prescribed target dose level for all the targets. In this approach, because the desired value for the target coverages is automatically attained, no plan normalization may be needed. Because the cost function is not in a closed functional form, the solution may depend on the path taken by the optimizer.

Figure 11:
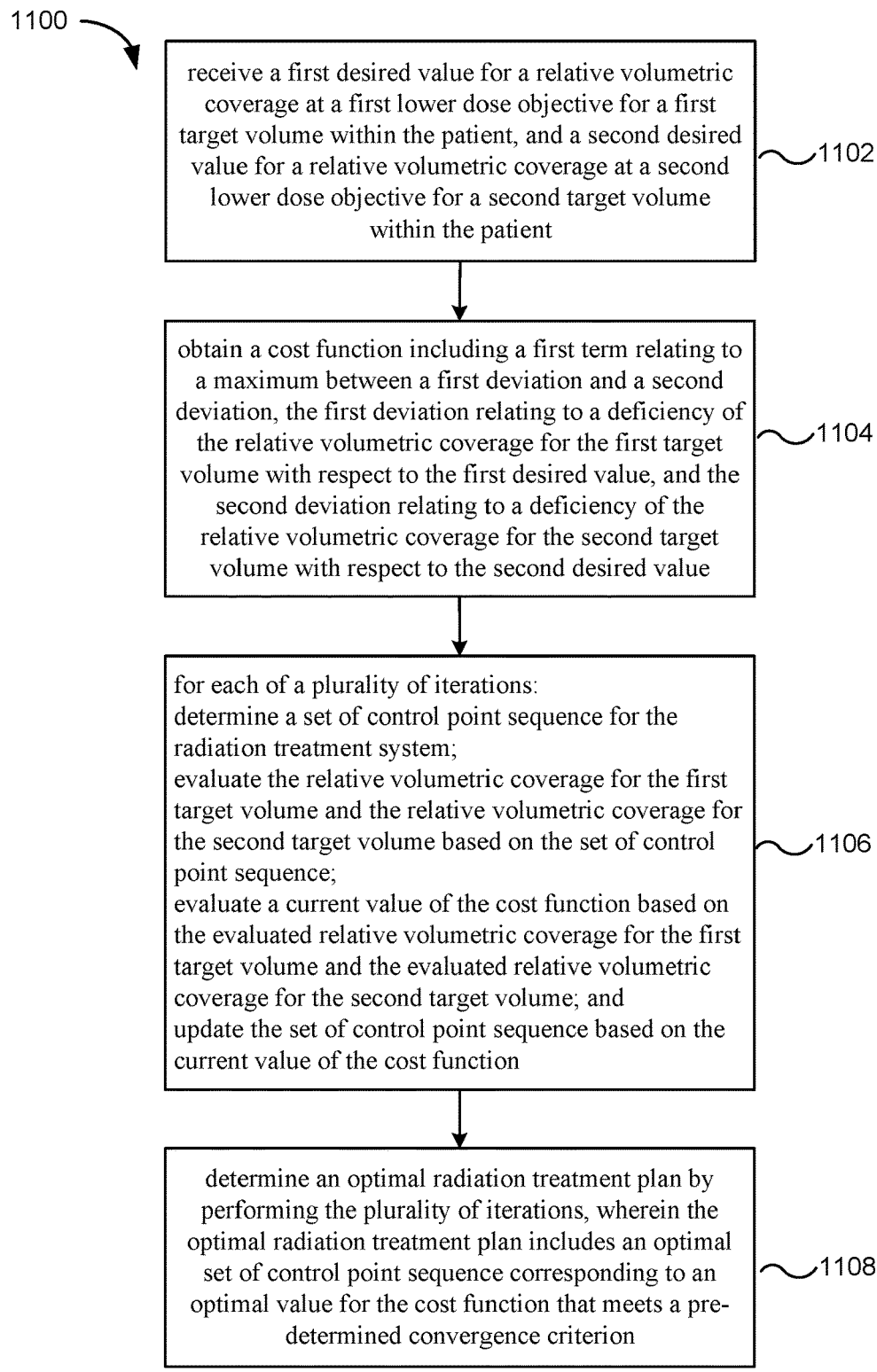
FIG. 11 is a simplified flowchart of a method of determining a radiation treatment plan for concurrent treatment of multiple target volumes according to some embodiments of the present invention.

IV. First Method of Determining Radiation Treatment Plans for Concurrent Treatment of Multiple Target Volumes FIG. 11 is a simplified flowchart of a method 1100 of determining a radiation treatment plan for concurrent treatment of multiple target volumes according to some embodiments.

At 1102, a first desired value for a relative volumetric coverage at a first lower dose objective for a first target volume within the patient, and a second desired value for a relative volumetric coverage at a second lower dose objective for a second target volume within the patient are received.

At 1104, a cost function is obtained. The cost function may include a first term relating to a maximum between a first deviation and a second deviation. The first deviation may relate to a deficiency of the relative volumetric coverage for the first target volume with respect to the first desired value. The second deviation may relate to a deficiency of the relative volumetric coverage for the second target volume with respect to the second desired value. For example, the cost function may have the form expressed in Eq. (2) as discussed above.

At 1106, for each of a plurality of iterations, a set of control point sequence for the radiation treatment system is determined. The relative volumetric coverage for the first target volume and the relative volumetric coverage for the second target volume are evaluated based on the set of control point sequence. A current value of the cost function is evaluated based on the evaluated relative volumetric coverage for the first target volume and the evaluated relative volumetric coverage for the second target volume. The set of control point sequence is then updated based on the current value of the cost function.

At 1108, an optimal radiation treatment plan is determined by performing the plurality of iterations. The optimal radiation treatment plan may include an optimal set of control point sequence that corresponds to an optimal value for the cost function. The optimal value for the cost function may meet a pre-determined convergence criterion.

Figure 12:
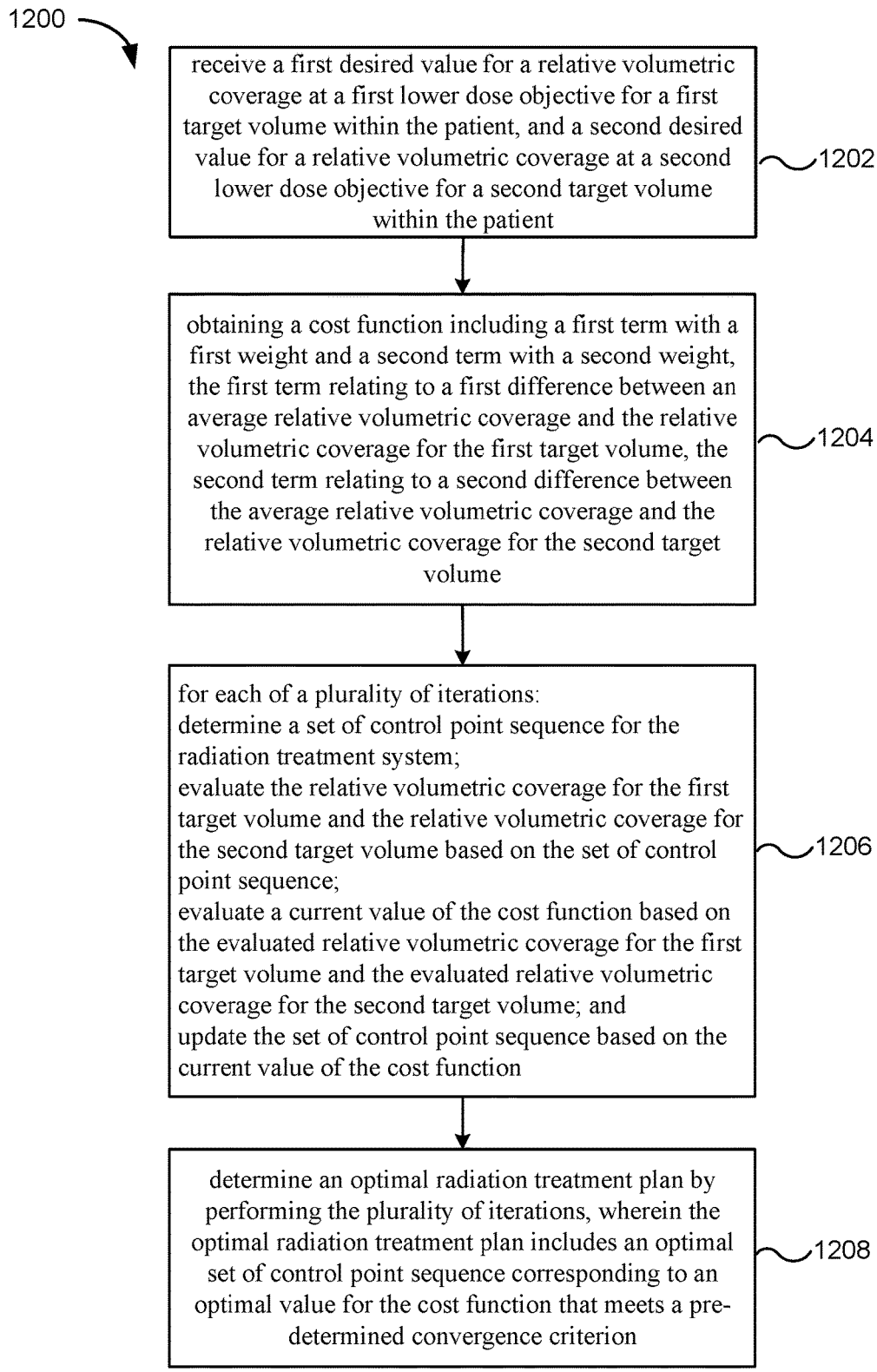
FIG. 12 is a simplified flowchart of a method of determining a radiation treatment plan for concurrent treatment of multiple target volumes according to some other embodiments of the present invention.

V. Second Method of Determining Radiation Treatment Plans for Concurrent Treatment of Multiple Target Volumes FIG. 12 is a simplified flowchart of a method 1200 of determining a radiation treatment plan for concurrent treatment of multiple target volumes according to some other embodiments.

At 1202, a first desired value for a relative volumetric coverage at a first lower dose objective for a first target volume within the patient, and a second desired value for a relative volumetric coverage at a second lower dose objective for a second target volume within the patient are received.

At 1204, a cost function is obtained. The cost function may include a first term with a first weight and a second term with a second weight. The first term may relate to a first difference between an average relative volumetric coverage and the relative volumetric coverage for the first target volume. The second term may relate to a second difference between the average relative volumetric coverage and the relative volumetric coverage for the second target volume. The average relative volumetric coverage is an average of the relative volumetric coverage for the first target volume and the relative volumetric coverage for the second target volume. For example, the cost function may have the form expressed in Eq. (3) as discussed above.

At 1206, for each of a plurality of iterations, a set of control point sequence for the radiation treatment system is determined. The relative volumetric coverage for the first target volume and the relative volumetric coverage for the second target volume are evaluated based on the set of control point sequence. A current value of the cost function is evaluated based on the evaluated relative volumetric coverage for the first target volume and the evaluated relative volumetric coverage for the second target volume. The set of control point sequence is then updated based on the current value of the cost function.

At 1208, an optimal radiation treatment plan is determined by performing the plurality of iterations. The optimal radiation treatment plan may include an optimal set of control point sequence that corresponds to an optimal value for the cost function. The optimal value for the cost function may meet a pre-determined convergence criterion.

Figure 13:
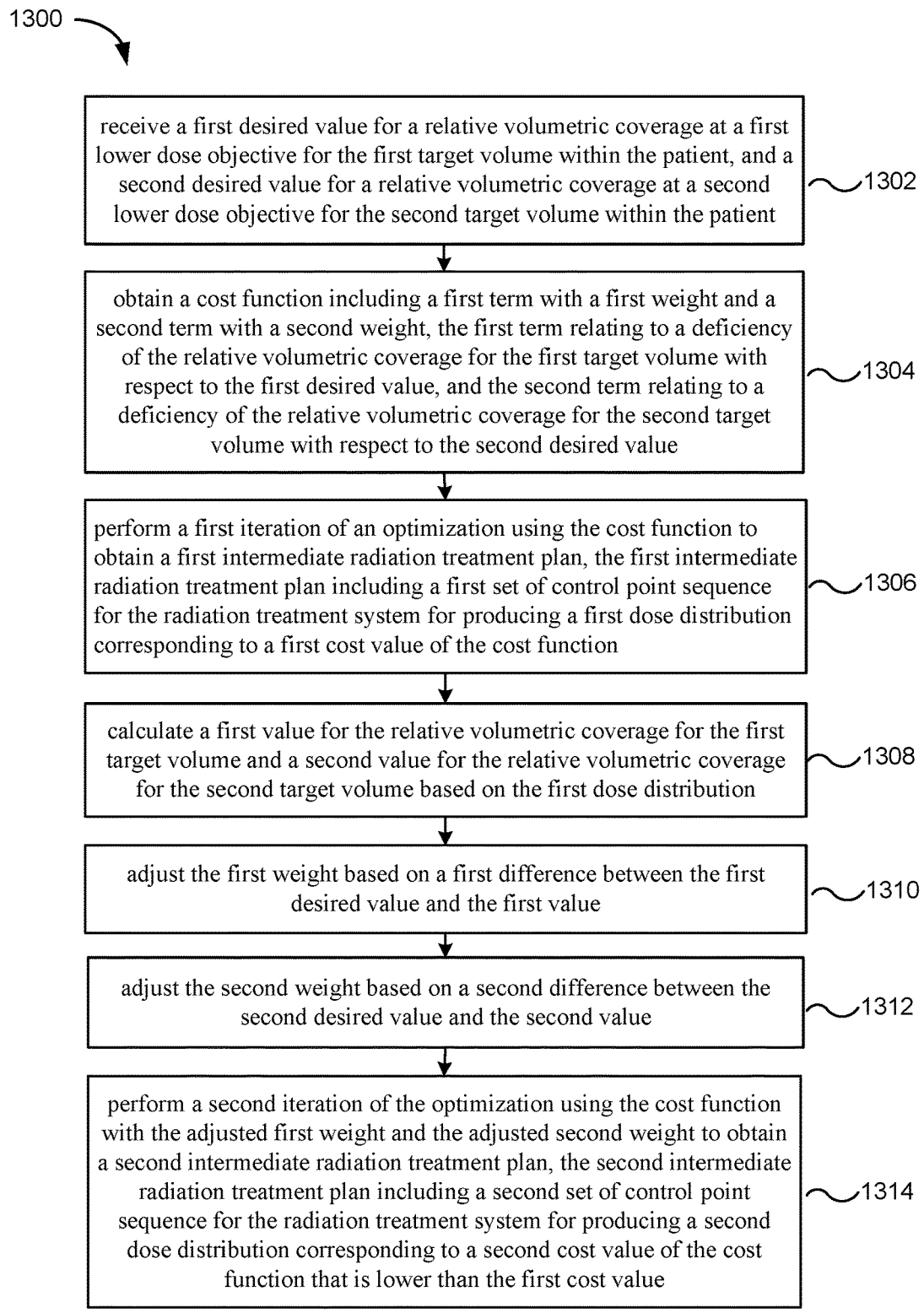
FIG. 13 is a simplified flowchart of a method of determining a radiation treatment plan for concurrent treatment of multiple target volumes according to some further embodiments of the present invention.

VI. Third Method of Determining Radiation Treatment Plans for Concurrent Treatment of Multiple Target Volumes FIG. 13 is a simplified flowchart of a method 1300 of determining a radiation treatment plan for concurrent treatment of multiple target volumes according to some further embodiments.

At 1302, a first desired value for a relative volumetric coverage at a first lower dose objective for the first target volume within the patient, and a second desired value for a relative volumetric coverage at a second lower dose objective for the second target volume within the patient are received.

At 1304, a cost function is obtained. The cost function may include a first term with a first weight and a second term with a second weight. The first term may relate to a deficiency of the relative volumetric coverage for the first target volume with respect to the first desired value. The second term may relate to a deficiency of the relative volumetric coverage for the second target volume with respect to the second desired value. For example, the cost function may have the form expressed in Eq. (1) as discussed above.

At 1306, a first iteration of an optimization is performed using the cost function to obtain a first intermediate radiation treatment plan. The first intermediate radiation treatment plan may include a first set of control point sequence for the radiation treatment system for producing a first dose distribution. The first dose distribution may correspond to a first cost value of the cost function.

At 1308, a first value for the relative volumetric coverage for the first target volume and a second value for the relative volumetric coverage for the second target volume are calculated based on the first dose distribution are calculated.

At 1310, the first weight may be adjusted based on a first difference between the first desired value and the first value. At 1312, the second weight may be adjusted based on a second difference between the second desired value and the second value. For example, the first weight and the second weight may be adjusted using the equations expressed in Eqs. (5)-(7) as discussed above.

At 1314, a second iteration of the optimization is performed using the cost function with the adjusted first weight and the adjusted second weight to obtain a second intermediate radiation treatment plan. The second intermediate radiation treatment plan may include a second set of control point sequence for the radiation treatment system for producing a second dose distribution. The second dose distribution may correspond to a second cost value of the cost function that is lower than the first cost value.

It should be appreciated that the specific steps illustrated in FIGS. 11-13 provide particular methods according to some embodiments of the present invention. For each of the methods, other sequences of steps may also be performed according to alternative embodiments. For example, alternative embodiments of the present invention may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

VII. Computer System

Figure 14:
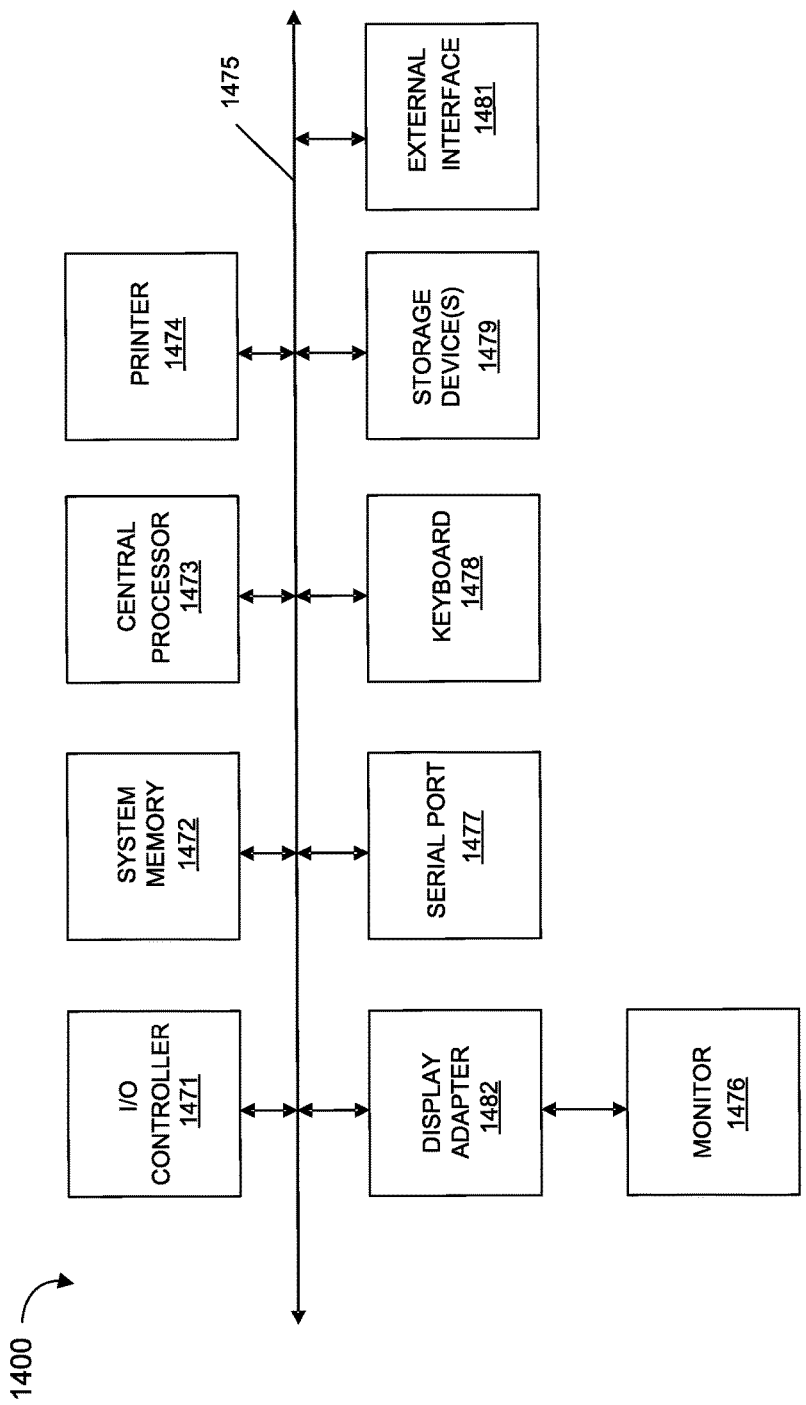
FIG. 14 shows a block diagram of an example computer system usable with system and methods according to embodiments of the present invention.

Any of the computer systems mentioned herein may utilize any suitable number of subsystems. Examples of such subsystems are shown in FIG. 14 in computer system 1400. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 14 are interconnected via a system bus 1475. Additional subsystems such as a printer 1474, keyboard 1478, storage device(s) 1479, monitor 1476, which is coupled to display adapter 1482, and others are shown. Peripherals and input/output (I/O) devices, which couple to I/O controller 1471, can be connected to the computer system by any number of means known in the art, such as serial port 1477. For example, serial port 1477 or external interface 1481 (e.g. Ethernet, Wi-Fi, etc.) can be used to connect computer system 1400 to a wide area network such as the Internet, a mouse input device, or a scanner. The interconnection via system bus 1475 allows the central processor 1473 to communicate with each subsystem and to control the execution of instructions from system memory 1472 or the storage device(s) 1479 (e.g., a fixed disk, such as a hard drive or optical disk), as well as the exchange of information between subsystems. The system memory 1472 and/or the storage device(s) 1479 may embody a computer readable medium. Any of the data mentioned herein can be output from one component to another component and can be output to the user.

A computer system can include a plurality of the same components or subsystems, e.g., connected together by external interface 1481 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a," "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of determining a radiation treatment plan for concurrent treatment of multiple target volumes within a patient using a radiation treatment system, the method comprising:
   receiving, at a computer system, a first desired value for a relative volumetric coverage at a first lower dose objective for a first target volume within the patient, and a second desired value for a relative volumetric coverage at a second lower dose objective for a second target volume within the patient;
   obtaining, by the computer system, a cost function including a first term relating to a maximum between a first deviation and a second deviation, the first deviation relating to a deficiency of the relative volumetric coverage for the first target volume with respect to the first desired value, and the second deviation relating to a deficiency of the relative volumetric coverage for the second target volume with respect to the second desired value;
   for each of a plurality of iterations:
      determining, by the computer system, a set of control point sequence for the radiation treatment system;
      evaluating, by the computer system, the relative volumetric coverage for the first target volume and the relative volumetric coverage for the second target volume based on the set of control point sequence;
      evaluating, by the computer system, a current value of the cost function based on the evaluated relative volumetric coverage for the first target volume and the evaluated relative volumetric coverage for the second target volume; and
      updating, by the computer system, the set of control point sequence based on the current value of the cost function; and
   determining, by the computer system, an optimal radiation treatment plan by performing the plurality of iterations, wherein the optimal radiation treatment plan includes an optimal set of control point sequence corresponding to an optimal value for the cost function that meets a pre-determined convergence criterion.

2. The method of claim 1, further comprising delivering radiation to the first target volume and the second target volume within the patient using the radiation treatment system according to the optimal set of control point sequence.

3. The method of claim 1, wherein the first deviation relates to square of the deficiency of the relative volumetric coverage for the first target volume with respect to the first desired value, and the second deviation relates to square of the deficiency of the relative volumetric coverage for the second target volume with respect to the second desired value.

4. The method of claim 1, wherein the first desired value is equal to the second desired value.

5. The method of claim 4, wherein the cost function includes one or more terms relating to one or more upper dose objectives for at least one of the first target volume, the second target volume, or an organ at risk (OAR).

6. A method of determining a radiation treatment plan for concurrent treatment of multiple target volumes within a patient using a radiation treatment system, the method comprising:

receiving, at a computer system, a first desired value for a relative volumetric coverage at a first lower dose objective for a first target volume within the patient, and a second desired value for a relative volumetric coverage at a second lower dose objective for a second target volume within the patient;

obtaining, by the computer system, a cost function including a first term with a first weight and a second term with a second weight, the first term relating to a first difference between an average relative volumetric coverage and the relative volumetric coverage for the first target volume, the second term relating to a second difference between the average relative volumetric coverage and the relative volumetric coverage for the second target volume, the average relative volumetric coverage being an average of the relative volumetric coverage for the first target volume and the relative volumetric coverage for the second target volume;

for each of a plurality of iterations:
   determining, by the computer system, a set of control point sequence for the radiation treatment system;
   evaluating, by the computer system, the relative volumetric coverage for the first target volume and the relative volumetric coverage for the second target volume based on the set of control point sequence;
   evaluating, by the computer system, a current value of the cost function based on the evaluated relative volumetric coverage for the first target volume and the evaluated relative volumetric coverage for the second target volume; and
   updating, by the computer system, the set of control point sequence based on the current value of the cost function; and determining, by the computer system, an optimal radiation treatment plan by performing the plurality of iterations, wherein the optimal radiation treatment plan includes an optimal set of control point sequence corresponding to an optimal value for the cost function that meets a pre-determined convergence criterion.

7. The method of claim 6, further comprising delivering radiation to the first target volume and the second target volume within the patient using the radiation treatment system according to the optimal set of control point sequence.

8. The method of claim 6, wherein the first term relates to an exponential function of the first difference, and the second term relates to an exponential function of the second difference.

9. The method of claim 6, wherein the first term of the cost function further relates to a deficiency of the relative volumetric coverage for the first target volume with respect to the first desired value, and the second term of the cost function further relates to a deficiency of the relative volumetric coverage for the second target volume with respect to the second desired value.

10. The method of claim 9, wherein the first term of the cost function relates to square of the deficiency of the relative volumetric coverage for the first target volume with respect to the first desired value, and the second term of the cost function relates to square of the deficiency of the relative volumetric coverage for the second target volume with respect to the second desired value.

11. The method of claim 6, wherein the first desired value is equal to the second desired value.

12. The method of claim 6, wherein the cost function further includes one or more terms relating to one or more upper dose objectives for at least one of the first target volume, the second target volume, or an organ at risk (OAR).

13. The method of claim 6, further comprising:
receiving, at the computer system, a third value for a lower dose objective for the first target volume, and a fourth value for a lower dose objective for the second target volume;
wherein the first term of the cost function further relates to a sum of a plurality of first deviations corresponding to a plurality of first sampling positions within the first target volume, each first deviation relating to a deficiency of a dose value at a respective first sampling position with respect to the third value; and
wherein the second term of the cost function further relates to a sum of a plurality of second deviations corresponding to a plurality of second sampling positions within the second target volume, each second deviation relating to a deficiency of a dose value at a respective second sampling position with respect to the fourth value.

14. A method of determining a radiation treatment plan for concurrent treatment of multiple target volumes within a patient using a radiation treatment system, the method comprising:
receiving, at a computer system, a first desired value for a relative volumetric coverage at a first lower dose objective for a first target volume within the patient, and a second desired value for a relative volumetric coverage at a second lower dose objective for a second target volume within the patient;
obtaining, by the computer system, a cost function including a first term with a first weight and a second term with a second weight, the first term relating to a deficiency of the relative volumetric coverage for the first target volume with respect to the first desired value, and the second term relating to a deficiency of the relative volumetric coverage for the second target volume with respect to the second desired value;
performing, by the computer system, a first iteration of an optimization using the cost function to obtain a first intermediate radiation treatment plan, the first intermediate radiation treatment plan including a first set of control point sequence for the radiation treatment system for producing a first dose distribution corresponding to a first cost value of the cost function;
calculating, by the computer system, a first value for the relative volumetric coverage for the first target volume and a second value for the relative volumetric coverage for the second target volume based on the first dose distribution;
adjusting, by the computer system, the first weight based on a first difference between the first desired value and the first value;
adjusting, by the computer system, the second weight based on a second difference between the second desired value and the second value; and
performing, by the computer system, a second iteration of the optimization using the cost function with the adjusted first weight and the adjusted second weight to obtain a second intermediate radiation treatment plan, the second intermediate radiation treatment plan including a second set of control point sequence for the radiation treatment system for producing a second dose distribution corresponding to a second cost value of the cost function that is lower than the first cost value.

15. The method of claim 14, further comprising:
performing, by the computer system, a number of iterations of the optimization using the cost function to obtain an optimal radiation treatment plan, wherein the optimal radiation treatment plan includes an optimal set of control point sequence corresponding to an optimal value for the cost function that meets a pre-determined convergence criterion; and
delivering radiation to the first target volume and the second target volume within the patient using the radiation treatment system according to the optimal set of control point sequence.

16. The method of claim 14, wherein adjusting the first weight is further based on a difference between an average relative volumetric coverage and the relative volumetric coverage for the first target volume, and adjusting the second weight is further based on a difference between the average relative volumetric coverage and the relative volumetric coverage for the second target volume, the average relative volumetric coverage being an average of the relative volumetric coverage for the first target volume and the relative volumetric coverage for the second target volume.

17. The method of claim 16, wherein the first desired value is equal to the second desired value.

18. The method of claim 17, further comprising:
adjusting, by the computer system, a total weight by a first amount based on a difference between the average relative volumetric coverage and the first desired value, the total weight being a sum of the first weight and the second weight;
wherein the first amount is less than a pre-determined percentage of the total weight.

19. The method of claim 14, further comprising:
receiving, at the computer system, a third value for a lower dose objective for the first target volume, and a fourth value for a lower dose objective for the second target volume;
wherein the first term of the cost function further relates to a sum of a plurality of first deviations corresponding to a plurality of first sampling positions within the first target volume, each first deviation relating to a deficiency of a dose value at a respective first sampling position with respect to the third value; and
wherein the second term of the cost function further relates to a sum of a plurality of second deviations corresponding to a plurality of second sampling positions within the second target volume, each second deviation relating to a deficiency of a dose value at a respective second sampling position with respect to the fourth value.

20. The method of claim 19, further comprising, before performing the second iteration of the optimization:
adjusting the third value based on a difference between the first desired value and the relative volumetric coverage for the first target volume; and
adjusting the fourth value based on a difference between the second desired value and the relative volumetric coverage for the second target volume.

* * * * *